United States Patent [19]
White et al.

[11] B 3,998,842
[45] Dec. 21, 1976

[54] DIAZEPINO[1,2-α]INDOLES

[75] Inventors: Alan Chapman White, Windsor; Robin Michael Black, Iver Heath, both of England

[73] Assignee: John Wyeth & Brother Limited, Maidenhead, England

[22] Filed: July 22, 1974

[21] Appl. No.: 490,812

[44] Published under the second Trial Voluntary Protest Program on March 30, 1976 as document No. B 490,812.

Related U.S. Application Data

[63] Continuation-in-part of Ser. No. 313,232, Dec. 8, 1972, Pat. No. 3,850,957.

[30] Foreign Application Priority Data

Dec. 14, 1971   United Kingdom .............. 1250/71

[52] U.S. Cl. ................. 260/326.5 B; 260/239 BC; 424/274
[51] Int. Cl.² ...................................... C07D 243/04
[58] Field of Search ............................ 260/326.5 B

[56] References Cited
UNITED STATES PATENTS
3,595,874   7/1971   Hester .................... 260/326.5 B

*Primary Examiner*—Paul M. Coughlan, Jr.

[57] ABSTRACT

This invention relates to bases of the formula

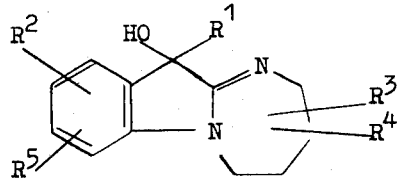

and their acid addition salts with pharmaceutically acceptable acids. In the formula $R^1$ represents phenyl or phenyl substituted by one or more hydroxyl, lower alkyl, lower alkoxy, haloloweralkyl or halogen atoms; $R^2$ and $R^5$ are hydrogen, hydroxyl, lower alkyl, lower alkoxy, haloloweralkyl or halogen and $R^3$ and $R^4$ are hydrogen or lower alkyl. The compounds have antidepressant activity.

5 Claims, No Drawings

DIAZEPINO[1,2-α]INDOLES

This application is a continuation-in-part of co-pending U.S. patent application Ser. No. 313,232 filed Dec. 8, 1972 entitled "Heterocyclic Compounds", now U.S. Pat. 3,850,957, granted Nov. 26, 1974.

The invention relates to diazepino]1,2-a]indoles, to processes for their preparation and to pharmaceutical compositions containing them.

The present invention provides a compound selected from the group consisting of bases having the formula

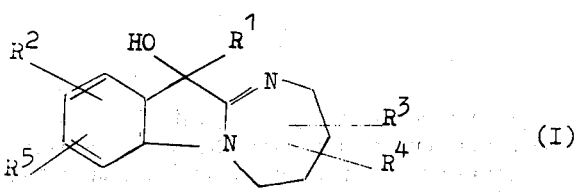

(I)

and the acid addition salts of said bases with pharmaceutically acceptable acids, wherein $R^1$ represents phenyl or phenyl substituted with one or more groups selected from hydroxyl, lower alkyl, lower alkoxy, haloloweralkyl and halogen; $R^2$ and $R^5$ are selected from the group consisting of hydrogen, hydroxyl, lower alkyl, lower alkoxy, haloloweralkyl and halogen; and $R^3$ and $R^4$ are selected from the group consisting of hydrogen and lower alkyl. The term "lower" as used herein means the radical contains up to 6, preferably up to 4 carbon atoms. It is to be understood that $R^3$ and $R^4$ may be on the same or different carbon atoms.

Since the compounds of the invention may possess one or more asymmetric carbon atoms, optical enantiomorphs are possible and the compounds of the invention may be the pure enantiomorphs or mixtures of such enantiomorphs, such as the racemates.

$R^1$ is a substituted or unsubstituted phenyl group. When the group is substituted suitable substituents are halogen (for example fluorine, chlorine or bromine), lower alkyl (for example methyl, ethyl, propyl, or butyl), lower alkoxy (for example methoxy, ethoxy, propoxy or butoxy) and haloloweralkyl (for example trifluoromethyl). The following are examples of residues for $R^2$ and $R^5$: lower alkyl residues, e.g. methyl, ethyl, propyl and butyl; lower alkoxy residues, e.g. methoxy, ethoxy, propoxy and butoxy; haloloweralkyl residues e.g. trifluoromethyl; and halogen groups e.g. chlorine and bromine. Preferably $R^2$ and $R^5$ are both hydrogen or one group is hydrogen and the other is, for example halogen. Examples of lower alkyl residues $R^3$ and $R^4$ are methyl, ethyl, propyl and butyl.

The preferred compounds are those of formula (I) in which $R^3$ and $R^4$ represent hydrogen atoms, $R^2$ and $R^5$ represent hydrogen atoms or halogen atoms and $R^1$ represents a phenyl, halophenyl or alkylphenyl radical. Examples of such preferred compounds are:

2,4,5,11-tetrahydro-11-phenyl-3H-1,3-diazepino[1,2-α]-indol-11-ol and
11-(m-chlorophenyl)-2,4,5,11-tetrahydro-3H-1,3-diazepino[1,2-α]indol-11-ol.

The compounds of the invention can be prepared by a process in which a ketone of formula (II)

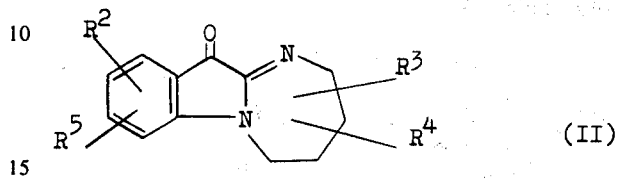

(II)

wherein $R^2$, $R^3$, $R^4$ and $R^5$ are as defined above, is reacted with an organometallic compound known in the art for the conversion of a ketone function to the group

and if desired a resulting base is converted to an acid addition salt with a pharmaceutically acceptable acid.

In the above process the organometallic compound is preferably chosen from (a) Grignard reagents of formula $R^1MgY$ wherein Y is halogen and $R^1$ has the meanings defined above, and (b) alkali-metal compounds such as the lithium derivatives of formula $R^1Li$ (particularly the aryl lithiums, for example phenyl lithium). The reaction with the organometallic compound is generally carried out in an inert organic solvent, for example ether or tetrahydrofuran, using the standard conditions known for the particular reaction concerned.

The ketone starting materials of the general formula (II) can be prepared by cyclisation of a ketone of formula (III)

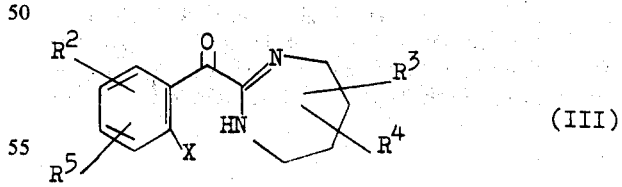

(III)

where $R^2$, $R^3$, $R^4$ and $R^5$ have the meanings given above and X is halo.

The ketone of formula (III) can be cyclised by a modified Ullmann Reaction. For example, the ketone may be treated with a metallic agent such as copper or a salt thereof, especially cupric oxide or cuprous chloride. The reaction is generally carried out in the presence of a base such as an alkaline metal carbonate (e.g. potassium carbonate), triethylamine or N-ethylmorpholine and preferably in a solvent (e.g. dimethylacetamide, pyridine, hexamethylphosphoric triamide or preferably dimethylformamide).

The group X is preferably bromo.

The ketones of general formula (III) can be prepared by oxidation of the corresponding hydroxy compounds of formula (IV)

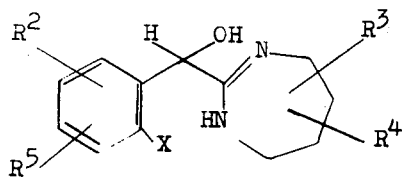

(IV)

wherein $R^2$, $R^3$, $R^4$, $R^5$, and X have the meanings given above. Preferably the oxidation is carried out with a mild oxidising agent such as manganese dioxide (for example, in solvents such as dichloromethane, chloroform, benzene, acetone or aqueous acetone).

The compounds of formula (IV) may be prepared by methods known in the literature such as the method described by Neilson et al., J. Chem. Soc.(C), 1968, 1853. For example 1,4-diaminobutane (the alkylene chain of which may be substituted by one or two lower alkyl groups) may be reacted with a lower alkyl imidate of formula

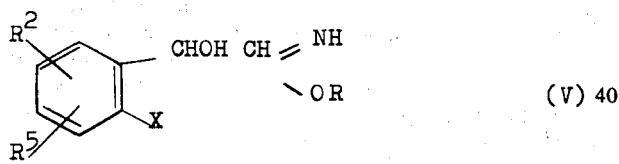

(V)

or an acid addition salt thereof (wherein $R^2$, $R^5$ and X are as defined above and R is a lower alkyl group).

The compounds of the invention can be prepared by an alternative process which comprises cyclodehydrating an indole derivative of the formula (VI)

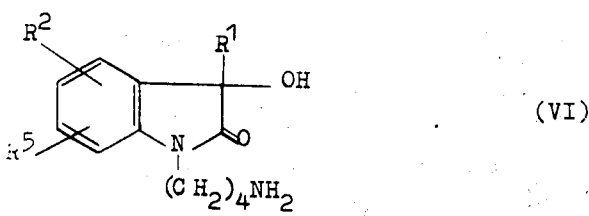

(VI)

wherein $R^1$, $R^2$ and $R^5$ have the meanings given above and if desired converting a resulting free base into an addition salt with a pharmaceutically acceptable acid.

The compound of formula (VI) may be cyclodehydrated by heating it, for example in an enert organic solvent. The solvent can be, e.g. xylene, or o-dichlorobenzene and the heating can be carried out at the reflux temperature. It is preferred to carry out the cyclodehydration in the presence of a catalytic amount of an acid catalyst, e.g. p-toluene sulphonic acid. Depending on the reaction conditions the cyclisation may be substantially complete in up to about 24 hours, e.g. up to 5 to 10 hours.

The indole derivatives of formula (VI) can be prepared by the hydrogenation of nitrile compounds of formula (VII)

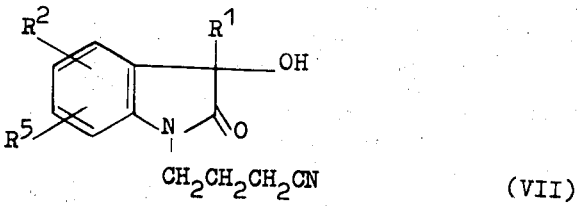

(VII)

wherein $R^1$, $R^2$ and $R^5$ have the meanings given above.

The hydrogenation is carried out in presence of a hydrogenation catalyst. Elevated temperatures and pressures may be employed. However, if the compound of formula (VII) contains any substituents such as halogen atoms, which are liable to be effected by drastic hydrogenation conditions, the hydrogenation should be carried out under mild conditions. For example, a nickel catalyst [such as Raney nickel, e.g. Raney nickel W2 (Org. Syn. Coll. Vol. III. 1955, 181)] can be employed, e.g. in presence of ammonia and ethanol, and the hydrogenation carried out at relatively low pressures (e.g. about 40 to 50 p.s.i.) and temperatures (e.g. about 40° to 50°C).

The compound of formula (VI) can be isolated from the reaction medium by standard procedures before cyclising it to the compound of formula (I). However such isolation is not necessary if it is desired to cyclodehydrate the compounds to the compounds of formula (I) directly.

The nitrile compounds of formula (VII) can be prepared by cyanopropylation of an oxindole of general formula (VIII)

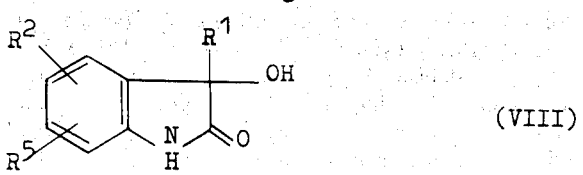

(VIII)

wherein $R^1$, $R^2$ and $R^5$ have the meanings given above. The cyanopropylation can be carried out, for example, by reacting the compound of formula (VIII) with a 4-halobutyronitrile, e.g. 4-bromobutyronitrile, in the presence of a base, e.g. sodium hydride, in an inert organic solvent, e.g. dimethylformamide, toluene or benzene.

The oxindoles of formula (VII) are known compounds or they may be prepared by known methods e.g. by reacting isatin or a substituted isatin with a Grignard reagent by the procedure given in Baumgarten et al., J. Amer. Chem. Soc., 1960, 82, 4634.

The compounds of formula (I) can be converted into their acid addition salts by standard procedures. For example, the free base can be dissolved in a suitable organic solvent and the solution treated with a solution of the selected acid, in accordance with conventional procedures for preparing acid addition salts from base compounds. Examples of suitable acids include hydrochloric, hydrobromic, tartaric, phosphoric, maleic, citric, methanesulphonic and p-toluenesulphonic acids.

The optical isomers of the compounds of formula (I) may be prepared by several processes. Preferably, a racemic mixture of a compound of the formula (I) is resolved by standard methods described in the literature. The racemate may be prepared by one of the processes outlined above.

Alternatively, an optically active isomer of a compound of the formula (I) can be prepared by any of the methods outlined above employing an optically active starting material, or a resolution can be carried out at any stage prior to formation of the compound of formula (I).

A resolution is preferably carried out on a racemic mixture of a basic compound of formula (I) by methods described in the literature, such as by use of an optically active acid. For instance, a solution of the racemate in a suitable solvent such as an alcohol is treated with a solution of an optically active acid to cause crystallisation of the salt of one particular enantiomorph. The other enantiomorph can often be obtained from the mother liquors, or if necessary by treatment with a base and then with the other optical isomer of the optically active acid, or alternatively a fresh solution of the racemate can be treated with a solution of the other enantiomorph of the optically active acid. The actual solvent and optically active acid to be used in any one instance can be determined by routine experiment. The best combination is that which allows the salt to be most easily isolated in a high state of purity (i.e. freedom from the other enantiomer) and in a crystalline form.

The compounds of the invention possess antidepressant activity, as indicated by standard pharmacological tests.

In one test the anti-depressant activity is measured by a procedure based upon that described by B. M. Askew in Life Sciences, 1963, 1, 725–730. In this procedure reserpine is administered to mice resulting in a decrease in their rectal temperature. The drug under test is administered subsequently and the rise in rectal temperature caused by the drug is compared with that in a control group. In this test compounds of the invention such as 11-(m-chlorophenyl)-2,4,5,11-tetrahydro-3H-1,3-diazepino-[1,2-$\alpha$]indol-11-ol and 2,4,5,11-tetrahydro-11-phenyl-3H-1,3-diazepino[1,2-$\alpha$]indol-11-ol show activity at doses as low as 9 mg/kg and even 3 mg/kg.

In an alternative procedure for measuring antidepressant activity, the inhibition of $^3$H-noradrenaline uptake in isolated rat brain slices is measured by a procedure similar to that described by L.L. Iversen et al in J. Neurochem., 1968, 15, 1141–1149. When tested in this way 11-(m-chlorophenyl)-2,4,5,11-tetrahydro-3H-1,3-diazepino[1,2-$\alpha$]indol-11-ol was approximately 1.4 times as potent as imipromine on a molar basis.

Some of the compounds of the invention also show hypoglycaemic acitvity when tested by a standard procedure in rats.

As the compounds of the invention show pharmaceutical activity the invention further provides a pharmaceutical composition which comprises a compound of formula (I) or its acid addition salt with a pharmaceutically acceptable acid in association with a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavoring agents, lubricants, solubilisers, suspending agents, binders or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch gelatin tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets, are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a coupound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule or tablet itself, or it can be the appropriate number of any of these in packaged form. The quantity of active ingredient in a unit dose of composition may be varied or adjusted from 5 mg. or less to 500 mg. or more, according to the particular need and the activity of the active ingredient. The invention also includes the compounds in the absence of carrier where the compounds are in unit dosage form.

The following Examples illustrate the invention:

EXAMPLE 1

11-(m-Chlorophenyl)-2,4,5,11-tetrahydro-3H-1,3-diazepino-[1,2-α]indol-11-ol a.

o-Bromophenyl-4,5,6,7-tetrahydro-1H-1,3-diazepino-2-methanol hydrochloride.

1,4-Diaminobutane (8.8g.) in absolute ethanol (10 ml) was added dropwise to a stirred, ice-cooled solution of ethyl o-bromomandelimidate hydrochloride (29.5 g.) in absolute ethanol (200 ml.). After the addition the mixture was stirred for a further hour with ice-bath cooling and then heated under reflux for 20hrs. After cooling the solution was concentrated under reduced pressure and ether added to give the white crystalline product (24.15g.) m.p. 213°–216°C(dec.). Recrystallisation from ethanol/ ether gave an analytical sample, m.p. 213°–216°(dec.).

Analysis: [FOUND C, 45.2; 4, 5.2; N, 9.0%; $C_{12}H_{15}BrN_2O\cdot HCl$ requires C, 45.1; H, 5.05; N, 8.75%].

b. o-Bromophenyl 4,5,6,7-tetrahydro-1H-1,3-diazepino-2-yl ketone.

A suspension of o-bromophenyl-4,5,6,7-tetrahydro-1H-1,3-diazepino-2-methanol hydrochloride (6.0 g.) in dry benzene (300 ml) was stirred with active manganese dioxide (50 g.) at room temperature for 60 hr. After filtering through kieselguhr the solvent was removed and the residue (2.274 g., m.p 57.60°C) crystallised from light petroleum (b.p. 60° – 80°C) after treatment with charcoal. Recrystallisation from light petroleum gave an analytical sample, m.p. 62° – 63°C.

Analysis: [FOUND C, 51.55; H, 4.8; N, 10.0%; $C_{12}H_{13}BrN_2O$ requires C, 51.25; H, 4.65; N, 9.95%].

c.
2,3,4,5-Tetrahydro-1,3-diazepino[1,2-α]indol-11-one

A solution of o-bromophenyl 4,5,6,7-tetrahydro-1H-1,3-diazepin-2-yl ketone (0.7 g.) in dry dimethylformamide (5 ml.) was stirred with potassium carbonate (0.35 g.) and cupric oxide (0.030 g.) at 90°C for 2 hr. under nitrogen. The mixture was diluted with benzene (100 ml.), filtered, washed with water (3 × 50 ml.) and dried over magnesium sulphate. After removal of the solvent under reduced pressure the residue was extracted with hot cyclohexane (ca.150 ml). The extracts slowly crystallised to give the 2,3,4,5-tetrahydro-1,3-diazepino[1,2-α]-indol-11-one as reddish-brown needles (0.179 g.) m.p. 137° – 139°C(dec.). An analytical sample was recrystallised from toluene, m.p. 140° – 141°C(dec.)

Analysis: [FOUND C, 72.0; H, 6.2; N, 13.75%; $C_{12}H_{12}N_2O$ requires C, 72.0; H, 6.05; N, 14.0%].

D.

11-(m-Chlorophenyl)-2,4,5,11-tetrahydro-3H-1,3-diazepino[1,2-α]indol-11-ol

A solution of 2,3,4,5-tetrahydro-1,3-diazepino-[1,2-α]indol-11-one (0.50 g.) in dry 1,2-dichloroethane (10 ml.) was added dropwise to a stirred, ice-cooled soln. of m-chlorophenylmagnesium bromide [made from m-bromochlorobenzene (1.44 g.) and magnesium (0.18 g.)]in dry ether (10 ml). After the addition the solution was stirred overnight at room temperature, poured onto ice/ammonium chloride solution and the organic phase separated. The aqueous phase was extracted with chloroform (2 × 20 ml.) and the combined extracts washed with water and dried over magnesium sulphate.

After removal of the solvent the residue was, taken up in isopropanol and carefully acidified with ethereal hydrochloric acid to give the crude hydrochloride of the title compound as yellowish needles (0.768 g.). Recrystallisation from isopropanol/methanol gave the pure hydrochloride of the title compound as colourless needles (0.639 g.), m.p. 261° – 265°C(dec.)

EXAMPLE 2

2,4,5,11-Tetrahydro-11-phenyl-3H-1,3-diazepino[1,2-α]-indol-11-ol

Reaction of 2,3,4,5-tetrahydro-1,3-diazepino-[1,2-α]indol-11-one with phenylmagnesium bromide by a procedure analogous to that described in procedure 1 (d) gives the hydrochloride of the title compound, m.p. 266° – 270°C(dec.).

In an analogous manner reaction of 2,3,4,5-tetrahydro-1,3-diazepino[1,2-α]indol-11-one with p-chlorophenylmagnesium bromide, m-methylphenylmagnesium bromide, m-methoxyphenyl magnesium bromide, m-trifluoromethylmagnesium bromide and 2,3-dichlorophenyl magnesium bromide gives respectively:
11-(p-chlorophenyl)-2,4,5,11-tetrahydro-3H-1,3-diazepino-[1,2-α]indol-11-ol
2,4,5,11-tetrahydro-11-(m-methylphenyl)-3H-1,3-diazepino-[1,2-α]indol-11-ol,
2,4,5,11-tetrahydro-11-(m-methoxyphenyl)-3H-1,3-diazepino-[1,2-α]indol-11-ol,
11-(m-trifluoromethylphenyl)-2,4,5,11-tetrahydro-3H-1,3-diazepino[1,2-α]indol-11-ol and
11-(2,3-dichlorophenyl)-2,4,5,11-tetrahydro-3H-1,3-diazepino[1,2-α]indol-11-ol.

EXAMPLE 3

11-(m-Chlorophenyl)-2,4,5,11-tetrahydro-3H-1,3-diazepino-[1,2-α]indol-11-ol. (alternative process)

a.
3-(m-Chlorophenyl)-3-hydroxy-2-oxo-1-indolinebutyronitrile 3-(m-Chlorophenyl)-3-hydroxy-2-indolinone (31.2g) in dry dimethylformamide (120 ml.) was added dropwise with stirring under nitrogen to a suspension of sodium hydride (5.2g of a 60% dispersion in oil) in dry dimethylformamide (120ml.) while keeping the temperature at 10°C. The reaction was then left stirring at room temperature for 1 hour. 4-Bromobutyronitrile (18.6g.) in dry toluene (120 ml.) was added dropwise and the mixture stirred for 36 hours. The reaction mixture was poured into water and extracted with toluene. The organic extracts were dried over magnesium sulphate and evaporated to an oil which afforded 21.3 g. colourless crystals, m.p. 124°–126°C, from ethanol.

Found: C, 65.6; H, 5.1; N, 8.1; $C_{18}H_{17}ClN_2O_2$ requires C, 65.75; H, 5.2; N, 8.5%).

b. 11-(m-Chlorophenyl)-2,4,5,11-tetrahydro-3H-[1,3]diazepino[1,2-α]indol-11-ol.

The nitrile from part (a) (1.52g.) was hydrogenated at 47 p.s.i. and 40°C in ethanol (50 ml.) half saturated with ammonia in the presence of Raney Nickel W2 (1 teaspoonful). After 6 hours the pressure drop corresponded to the adsorption of the theoretical quantity of hydrogen. The catalyst was filtered off and the ethanol was removed to leave an oil which was heated for 6 hours under reflux in xylene containing a catalytic quantity of toluene-p-sulphonic acid, azeotropically removing the small amount of water formed. The dark solution was decolourised with charcoal and the xylene removed under reduced pressure to leave a pale yellow oil. On treatment with isopropanol/ethereal hydrogen chloride the hydrochloride of the title compound was obtained as pale yellow needles (545 mg.) m.p. 259°–262°C (decomp.)- Colourless needles, m.p. 262°–266°C(decomp.), were obtained on recrystallisation from an isopropanol/ethanol mixture.

(Found: C, 61.75; H, 5.4; N, 7.75; $C_{18}H_{17}ClN_2O$ HCl requires C, 61.9; H, 5.2; N, 8.0%).

EXAMPLE 4

Reaction of 5-chloro-3-hydroxy-3-phenyl-2-indolinone with 4-bromobutyronitrile by a procedure analogous to that in Example 3(a) followed by hydrogenation of the resulting nitrile by a procedure analogous to that of Example 3(b) gives 9-chloro-11-phenyl-2,4,5,11-tetrahydro-3H-1,3-diazepino[1,2-α)indo-11-ol [m.p. of hydrobromide is 298°–300°C(decomp.)].

Similarly, reaction of 5-chloro-3-(o-chlorophenyl)-3-hydroxy-2-indolinone with 4-bromobutyronitrile by a procedure analogous to that in Example 3(a) followed by hydrogenation of the resulting nitrile by a procedure analogous to that of Example 3(b) gives 9-chloro-11-(o-chlorophenyl)-2,4,5,11-tetrahydro-3H-1,3-diazepino-[1,2-α]indol-11-ol [m.p. of the hydrobromide is 295°–300°C (decomp)].

We claim:

1. A compound selected from the group consisting of bases having the formula:

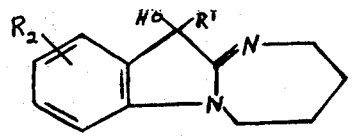

and the acid addition salts of said bases with pharmaceutically acceptable acids, wherein $R^1$ represents a member of the group consisting of phenyl, halophenyl, lower alkyl phenyl, lower alkoxy phenyl, dihalophenyl and trifluoromethylphenyl; and $R^2$ is halogen or hydrogen.

2. The compound according to claim 1 which is 2,4,5,11-tetrahydro-11-phenyl-3H-1,3-diazepino[1,2-α]indol-11-ol.

3. The compound according to claim 1 which is 11-(m-chlorophenyl)-2,4,5,11-tetrahydro-3H-1,3-diazepino-[1,2-α]indol-11-ol.

4. The compound according to claim 1 which is 9-chloro-11-phenyl-2,4,5,11-tetrahydro-3H-1,3-diazepino-[1,2-α]indol-11-ol.

5. The compound according to claim 1 which is 9-chloro-11-(o-chlorophenyl)-2,4,5,11-tetrahydro-3H-1,3-diazepino[1,2-α]indol-11-ol.

* * * * *